United States Patent [19]
Früh et al.

[11] Patent Number: 6,136,987
[45] Date of Patent: Oct. 24, 2000

[54] USE OF ARYLGUANIDINIUM XANTHOGENATES AS VULCANIZATION ACCELERATORS AND PROCESS FOR THE PRODUCTION THEREOF

[75] Inventors: Thomas Früh, Ludwigshafen; Ludger Heiliger, Neustadt; Hermann Lohwasser, Stockach, all of Germany

[73] Assignee: Rhein Chemie Rheinau GmbH, Mannheim, Germany

[21] Appl. No.: 09/426,037

[22] Filed: Oct. 25, 1999

[30] Foreign Application Priority Data

Oct. 29, 1998 [DE] Germany .......................... 198 49 818

[51] Int. Cl.⁷ ........................ C07D 307/02; C07C 281/00
[52] U.S. Cl. .................... 549/475; 564/227; 564/228
[58] Field of Search ...................................... 564/227, 288; 549/475

[56] References Cited

U.S. PATENT DOCUMENTS

| 3,683,023 | 8/1972 | Winter et al. | 564/227 |
| 4,015,016 | 3/1977 | Livak et al. | 564/227 |
| 5,296,498 | 3/1994 | Malen et al. | 564/227 |

*Primary Examiner*—Amelia Owens
*Attorney, Agent, or Firm*—Joseph C. Gil; Noland J. Cheung

[57] ABSTRACT

This invention relates to the use of arylguanidinium xanthogenates as vulcanization accelerators, to a process for the production thereof and to the arylguanidinium xanthogenates.

6 Claims, No Drawings

USE OF ARYLGUANIDINIUM XANTHOGENATES AS VULCANIZATION ACCELERATORS AND PROCESS FOR THE PRODUCTION THEREOF

FIELD OF THE INVENTION

This invention relates to the use of arylguanidinium xanthogenates as vulcanization accelerators and to a process for the production thereof.

BACKGROUND OF THE INVENTION

Unsaturated rubbers are vulcanized using not only sulfur, but also vulcanization accelerators. These are selected depending upon the intended application and desired characteristics of the rubber. Groups of accelerators, which have differentiated properties within each group, are, for example, thittram disulfides, dithiocarbamates, benzothiazolesulfenamides, N-arylguanidines, some amines, polyamrines, thioureas and derivatives of dialkylthiophosphoric acids, such as O,O-dialkyldithio-phospliate metal salts.

The complex salt prepared from N,N'-diphenylguanidine, boric acid and pyrocatechol (DBB) is one specific accelerator compound. This comiipouiid has only moderate acceleration action.

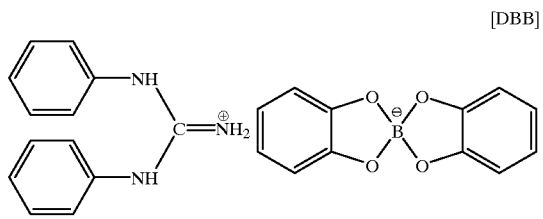

[DBB]

The added accelerators undergo change on vulcanization. In many cases, secondary amines are formed, which form nitrosamines with nitrosamine-foirmers from the environment (for example, atmospheric $NO_x$, nitrite in the solids). Nitrosamines are considered carcinogenic, such that the formation thereof during rubber vulcanization is unwanted.

SUMMARY OF THE INVENTION

The object of the invention is to provide highly effective accelerators for vulcanizing rubbers which may be used without any risk of nitrosamine formation.

DETAILED DESCRIPTION OF THE INVENTION

The present invention provides the production and use of arylguanidinium xanthogenates as ultra-accelerators for rubber vulcanization (diene rubbers). The arylguanidinium xanthogenates are of the formula (I)

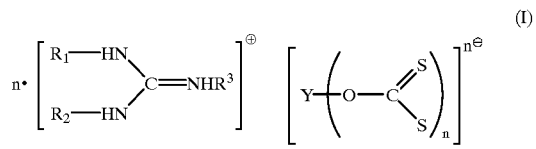

(I)

in which

Y is a hydrocarbon residue derived from a mono- or polyhlydric alcohol, wherein the residue may optionally contain heteroatoms such as oxygen, sulfur or nitrogen, or, as a monomer unit, is part of a polymer $(P=Y_x)$, where x=2 to 5000.

n is an integer from 1 to 6, preferably from 1 to 3, particularly preferably 1 or 2, or it Y represents a monomer unit of a polymer.

n is an integer from 2 to 20000, preferably from 2 to 1000, $R^1$, $R^2$ and $R^3$ is aryl or hydrogen, wherein at least one of $R^1$, $R^2$ or $R^3$ is aryl.

The arylguanidinium xanthogenates, bisxanthogenates and polyxanthoglenates according to the present invention of the formula (I) form no N-nitrosamines and, unlike other known accelerators, also contain no heavy metals in the molecule. They carry good accelerators.

Aryl is preferably $C_6$–$C_{10}$ aryl, in particular phenyl. The substituent Y is preferably an alkyl residue having 2 to 10 carbon atoms, an alkylene residue radical having 2 to 10 cardon atoms, an oxyalkylene residue or benzyl or a natural polyhydric compound derived poly-radical.

N,N'-Diarylguanidinium xanthogenates of the formula (I) are shown in Table 1, which have the following particularly preferred compositions are used:

TABLE 1

| Accelerator compound (I) | Substituent Y | Substituent $R^1 = R^2$ with $R^3 = H$ |
| --- | --- | --- |
| 1 | isopropyl | phenyl |
| 2 | isopropyl | o-tolyl |
| 3 | isopropyl | p-chlorophenyl |
| 4 | n-butyl | phenyl |
| 5 | isobutyl | phenyl |
| 6 | sec.-butyl | phenyl |
| 7 | cyclohexyl | phenyl |
| 8 | benzyl | phenyl |
| 9 | 1,2-ethylene | phenyl |
| 10 | 1-methyl-1,2-ethylene | phenyl |
| 11 | 1,1-dimethyl-1,2-ethylene | phenyl |
| 12 | 1,2-dimethyl-1,2-ethylene | phenyl |
| 13 | 1,3-propylene | phenyl |
| 14 | 2-hydroxy-1,3-propylene | phenyl |
| 15 | 2,2'-oxydiethylene | phenyl |

The compounds of the formula (I) may be used alone or in combination with secondary accelerators, preferably also for post-vulcanizing chemically, mechanically or electro-magnetically degraded primary vulcanizates (recycled materials).

The arylguanidinium xanthogenates may be produced by reacting a corresponding amino compound with cyanogen chloride (in liquid or vapor form) in an inert organic solvent until a diarylguanidinium hydrochloride has formed quantitatively. Once combined with water, this intermediate product dissolves in the aqueous phase, is separated from the organic phase, optionally filtered and combined with an aqueous alkali metal (poly)xanthogenate solution. The products (I) crystallize out from the concentrated reaction solutions or are precipitated as amorphous precipitates.

Example with aniline:

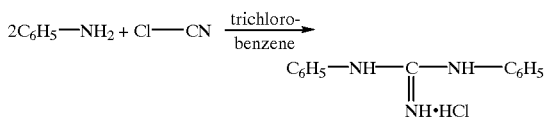

diphenylguanidinium hydrochloride

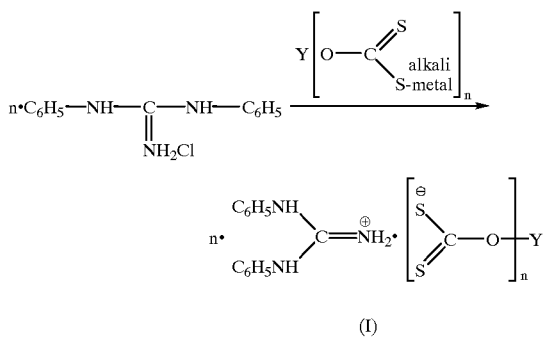

(I)

The diarylguanidiniumii hydrochlor-ide may also be produced by dissolving the diarylgiuainidine in dilute hydrochloric acid. The water-insoluble product (I) according to the invention is then obtained therefrom by anion exchange.

Triarylguanidinium xanthogenates according to the invention may, for example, be produced by initially synthesizing the corresponding N,N',N"-triarylguanidinium salt from the primary arylamine and reacting this synthesis product within alkali metal (poly)xanthogenates:

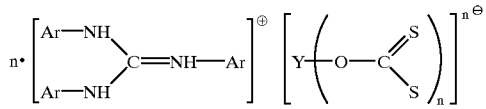

Xanthogenate derivatives of natural products or of modified natural products of the polysaccharide series or derivatives of polyvinyl alcohol or the copolymers thereof may also be produced in the above-stated manner. Examples which may be mentioned are:

[cellulose-$(OCS_2)_m]^{m\ominus} \cdot m[(ArNH)_2C=NHR^3]^{\oplus}$
[starch-$(OCS_2)_n]^{n\ominus} \cdot n[(ArNH)_2C=NHR^3]^{\oplus}$
[hydroxymethylcellulose-$(OCS_2)_p]^{p\ominus} \cdot p[(ArNH)_2C=NHR^3]^{\oplus}$
[hydroxyethylstarch-$(OCS_2)_q]^{q\ominus} \cdot q[(ArNH)_2C=NHR^3]^{\oplus}$
poly[vinyl alcohol-$(OCS_2)_r]^{r\ominus} \cdot r[(ArNH)_2C=NHR^3]^{\oplus}$ where m, n, p, q and r are integers from 1 to 4, relative to the monomeric unit of the polymer.

In comparison with other nitrosamine-free accelerator systems, different scorch times and lower viscosities of the compounds may be achieved. Depending upon how the compound is processed, this may amount to a distinct improvement. Vulcanizate properties can satisfy an extensive range of requirements by using this new class of substances, which cannot be satisfied by using comparison substances.

The following Examples are intended to illustrate the invention.

EXAMPLES 1–3 (Production Examples)

Example 1

A solution of N,N'-diphenylcuanidinium hydrochloride is produced by dissolving N,N'-diphenylguanidinium in dilute hydrochloric acid or is produced in situ in an organic phase from aniline or aniline hydrochloride and cyanocen chloride and then converted into an aqueous phase.

An equivalent quantity of a dilute alkaline solution of sodium isopropylxanthogenate (Proxan-Na) is slowly introduced into this solution with stirring and cooling. A dense white precipitate of N,N'-diphenylguanidinium O-isopropylxanthogenate rapidly forms in a virtually quantitative yield, and is filtered, washed and dried.

Elemental Analysis

| | calculated: | actual: |
|---|---|---|
| C: | 58.8% | 57.8% |
| H: | 6.1% | 6.2% |
| N: | 12.1% | 11.7% |
| S: | 18.4% | 18.2% |
| m.p.: 103–106° C. | | |

Example 2

In a corresponding manner to Example a), an aqueous solution of N,N'-diortho-tolylguanidinium hydrochloride and an aqueous solution of the potassium salt of glycerol 1,3-bis-xanthogenatc are cautiously mixed together in a molar ratio of 2:1.

Bis-(N,N'-ditolylguanidinium)-2-hydroxy-1,3-propylene bisxanthogenate is formed in a quantitative yield (N: calc. 10.2%, actual 10.4%; S: calc. 14.4%, actual 14.1%).

Example 3

An aqueous solution of polyvinyl alcohol is reacted in a known manner with sodium hydroxide solution and carbon disulfide ($CS_2$) to yield a polyxanthogenate solution. The equivalent molar quantity, relative to $CS_2$, of N,N'-diphenylguanidinium hydrogen sulfate is cautiously stirred into this initial mixture.

A voluminous precipitate of the diphenylguanidinium polyvinvlxarn-thogenate is obtained which, after filtration and washing twice with water, is dried to constant weight [N: calc. 12.7%, actual 11.4%; S: calc. 19.4%, actual 18.1%]. This corresponds to a degree of conversion of approx. 60 to 70%.

EXAMPLES 4–6 (Practical Examples)

Example 4

1.1 phr (parts per hundred rubber) of a mixture of commercially available accelerators (see Table 2) or 1.1 phr of the product from Example 1 (diphenylguanidiniium isopropylxanthogenate) were added to a rubber compound (see Table 2).

The product from Example 1 (diplhenylguanidinium isopropylxan-thogenate) exhibits a greater crosslinking yield (Fmax-Fmin values in Nm). It may be concluded from the higher Vmax values that crosslinking is more efficient.

On roll/flex testing, the product from a) (diphenylguanidiniunm isopropyl-xanthogenate) exhibits lower "heat build up" (T values, 90° flexure angle). In this test, the surface temperature of the rubber specimen is measured under dynamic load (frequency of rotation 1400 Hz). This value may be of significance, for example, in the production of drive belts.

Both before and after heat aging, the physical properties hardness (° Sheore A), tear propagation strength, tensile strength and 100 and 300 modulus values (force at 100% and 300% longitudinal strain extension) are more favorable for product from Example 1 than for the comparison compound. This improvement is also largely retained during the aging process. The same applies to elongation at break.

Vulcanization without using zinc oxide (Example 5) gives rise to vulcanizate properties of a comparable order of magnitude to vulcanization with zinc oxide (Example 6). The same applies to the rheometer testing. It is very rare for vulcanization accelerators to make it possible to dispense with using zinc oxide.

TABLE 2

| Applicational data | 4 | 5 | 6 |
|---|---|---|---|
| SMR CV 50 (parts by weight) | 100 | 100 | 100 |
| CN N 550 (parts by weight) | 50 | 50 | 50 |
| Naphthenic petroleum (parts by weight) | 5 | 5 | 5 |
| Stearic acid (parts by weight) | 1 | 1 | 1 |
| ZnO spec. (parts by weight) | 2.5 | 2.5 | — |
| Vulkanox 4020 (parts by weight) | 2 | 2 | 2 |
| Rhenogran S-80 (parts by weight) | 2 | 2 | 2 |
| Vulkacit D (guanidine) (parts by weight) | 0.6 | — | — |
| Sodium isopropylxanthogenate (parts by weight) | 0.5 | — | — |
| Product from example 1) (parts by weight) | — | 1.1 | 1.1 |
| Mooney ML 1 + 4/ 100° C. to DIN 53 523 | 43 | 53 | 56 |
| Mooney scorch 120° C. to DIN 53 523 | | | |
| t5 (min) | 7.82 | 7.62 | 11.08 |
| t35 (min) | 14.85 | 11.47 | >60 |
| Vulkameter: 160° C. to DIN 53 529 | | | |
| t10 (min) | 0.8 | 0.8 | 0.8 |
| t50 (min) | 2.7 | 2.4 | 3.6 |
| t90 (min) | 9.5 | 9.6 | 13 |
| Vmax (Nm/min) | 0.08 | 0.1 | 0.08 |
| Fmax-Fmin (Nm) | 0.28 | 0.29 | 0.24 |
| Vulkameter: 170° C. to DIN 53 529 | | | |
| t10 (min) | 0.6 | 0.6 | 0.6 |
| t50 (min) | 1.3 | 1.2 | 1.5 |
| t90 (min) | 3.7 | 3.7 | 5 |
| Vmax (Nm/min) | 0.13 | 0.18 | 0.12 |
| Fmax-Fmin (Nm) | 0.24 | 0.3 | 0.24 |
| Vulkameter: 180° C. to DIN 53 529 | | | |
| t10 (min) | 0.5 | 0.5 | 0.5 |
| t50 (min) | 0.9 | 0.8 | 1 |
| t90 (min) | 1.8 | 1.8 | 2.5 |
| Vmax (Nm/min) | 0.19 | 0.24 | 0.17 |
| Fmax-Fmin (Nm) | 0.22 | 0.29 | 0.24 |
| Roll/flex, 90° | | | |
| T after 5' | 125 | 105 | 98 |
| T after 10' | 134 | 120 | 121 |
| T after 15' | 136 | 125 | 125 |
| T after 20' | 138 | 126 | 127 |
| Vulcanization: 170° C. | | | |
| Density (g/mm³) | 1.11 | | |
| Hardness (° Shore A) | 38 | 43 | 41 |
| Elasticity (%) | 46 | 45 | 47 |
| Tear propagation strength (N/mm) | 8.27 | 9.48 | 8.57 |

TABLE 2-continued

| Applicational data | 4 | 5 | 6 |
|---|---|---|---|
| Modulus 100 (MPa) | 1.2 | 1.5 | 0.9 |
| Modulus 300 (MPa) | 5.7 | 6.6 | 3.4 |
| Modulus 500 (MPa) | — | — | 7.6 |
| Tensile strength (MPa) | 10.1 | 12.4 | 8.1 |
| Elongation at break (%) | 463 | 484 | 522 |
| Bloom | no | no | no |
| Hot air aging: 3 d/70° C. (vulcanization at 170° C.) | | | |
| Hardness (° Shore A) | 50 | 53 | 58 |
| Elasticity (%) | 41 | 42 | 43 |
| Tear propagation strength (N/mm) | 7.1 | 7.2 | 6.8 |
| Modulus 100 (MPa) | 4.2 | 3.1 | 3.6 |
| Modulus 300 (MPa) | — | — | — |
| Modulus 500 (MPa) | — | — | — |
| Tensile strength (MPa) | 4.5 | 5.7 | 6.3 |
| Tensile strength retention (%) | 45 | 46 | 78 |
| Elongation at break (%) | 102 | 165 | 160 |
| Elongation at break retention (%) | 22 | 34 | 31 |
| Bloom | no | no | no |
| Hot air aging: 7 d/100° C. (vulcanization at 170° C.) | | | |
| Hardness (° Shore A) | 56 | 57 | 59 |
| Elasticity (%) | 39 | 38 | 41 |
| Tear propagation strength (N/mm) | 6.13 | 5.95 | 7.12 |
| Modulus 100 (MPa) | 3.7 | 3.5 | 3.7 |
| Modulus 300 (MPa) | — | — | — |
| Modulus 500 (MPa) | — | — | — |
| Tensile strength (MPa) | 5.7 | 7.1 | 7.7 |
| Tensile strength retention (%) | 56 | 57 | 95 |
| Elongation at break (%) | 168 | 222 | 236 |
| Elongation at break retention (%) | 36 | 46 | 45 |
| Bloom | no | no | no |

SMR CV 50: Standard Malaysian Rubber, constant viscosity 50, in accordance with Malaysian Rubber Bureau (MRB) specification.

CN N 550: Carbon black N 550

Vulkanox® 4020: Antioxidant of Bayer AG (N-(1,3-dimethylbutyl)-N'-phenylparaphenylenediamine)

Rhenogran® S-80: Commercial product of Rhein Chemie Rheinau GmbH (polymer-bound sulfur with 80% active substance content)

Vulkacit® D: Diphenylguanidine; commercial product of Bayer AG

Mooney scorch Determination of Mooney scorch behavior

120° C.: t5 and t35 are determined at a specified temperature (120° C.)

Vulkameter: Apparatus for determining crosslinking behavior; vulkametry performed to DIN 53 529

Vulcanization: Vulcanization was performed under pressure and at a temperature of 170° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A vulcanization accelerator for rubber comprising arylguanidinium xanthogenates of the formula (I)

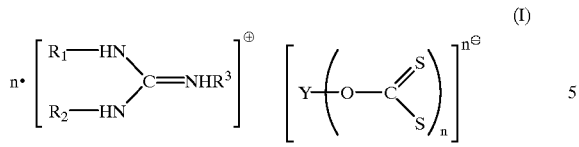

(I)

in which

R¹, R² and R³ are aryl residues or hydrogen, wherein at least one of R¹, R² or R³ is an aryl residue, n is an integer from 1 to 6, or if Y represents a monomer unit of a polymer, n is an integer from 2 to 20,000, Y is a hydrocarbon residue derived from a mono- or polyhydric alcohol, wherein said residue may optionally contain heteroatoms, such as oxygen, sulfur or nitrogen, or, as a monomer unit, is part of a polymer ($P=Y_x$), wherein x ranges from 2 to 5000.

2. A vulcanization accelerator for rubber according to claim 1, wherein said rubber is a diene rubber.

3. A vulcanization accelerator for rubber according to claim 1, wherein said diarylguanidinium xanthogenates of the formula (I) have the following compositions:

| Accelerator compound (I) | Substituent Y | Substituent R¹ = R² with R³ = H |
|---|---|---|
| 1 | isopropyl | phenyl |
| 2 | isopropyl | o-tolyl |
| 3 | isopropyl | p-chlorophenyl |
| 4 | n-butyl | phenyl |
| 5 | isobutyl | phenyl |
| 6 | sec.-butyl | phenyl |
| 7 | cyclohexyl | phenyl |
| 8 | benzyl | phenyl |
| 9 | 1,2-ethylene | phenyl |
| 10 | 1-methyl-1,2-ethylene | phenyl |
| 11 | 1,1-dimethyl-1,2-ethylene | phenyl |
| 12 | 1,2-dimethyl-1,2-ethylene | phenyl |
| 13 | 1,3-propylene | phenyl |
| 14 | 2-hydroxy-1,3-propylene | phenyl |
| 15 | 2,2'-oxydiethylene | phenyl |

4. A vulcanization accelerator for rubber according to claim 1, wherein said vulcanization accelerator is used in combination with known secondary accelerators for vulcanizing rubbers.

5. A process for the production of arylguanidinium xanthogenates of the formula (I)

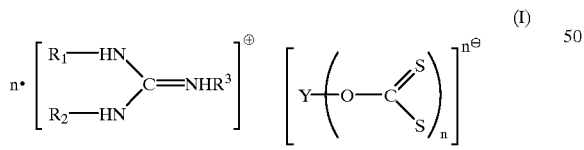

(I)

by reacting salts of arylguanidinium (II) with xanthogenate salts (III)

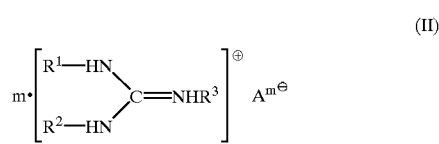

(II)

where A is Cl, $SO_4$, $PO_4$ or acetate and m is from 1 to 3,

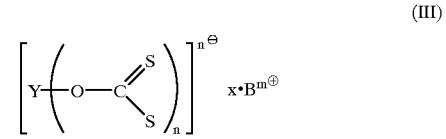

(III)

where B is alkali metal or an alkaline earth metal and m is 1 or 2 and x=n/m, wherein R¹, R² and R³ are aryl residues or hydrogen, wherein at least one of R¹, R² or R³ is an aryl residue, n is an integer from 1 to 6, or if Y represents a monomer unit of a polymer, n is an integer from 2 to 20,000, Y is a hydrocarbon residue derived from a mono- or polyhydric alcohol, wherein said residue may optionally contain heteroatoms, such as oxygen, sulfur or nitrogen, or, as a monomer unit, is part of a polymer ($P=Y_x$), wherein x ranges from 2 to 5000.

6. Arylguanidinium xanthogenates of the formula (I)

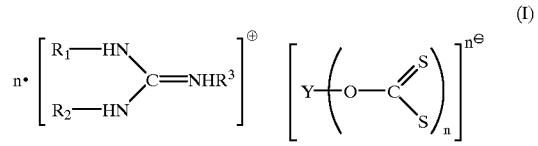

(I)

wherein R¹, R² and R³ are aryl residues or hydrogen, wherein at least one of R¹, R² or R³ is an aryl residue, n is an integer from 1 to 6, or if Y represents a monomer unit of a polymer, n is an integer from 2 to 20,000, Y is a hydrocarbon residue derived from a mono- or polyhydric alcohol, wherein said residue may optionally contain heteroatoms, such as oxygen, sulfur or nitrogen, or, as a monomer unit, is part of a polymer ($P=Y_x$), wherein x ranges from 2 to 5000.

* * * * *